(12) United States Patent
Stratmann

(10) Patent No.: US 9,176,034 B2
(45) Date of Patent: Nov. 3, 2015

(54) OBJECT SUPPORT RETAINER

(75) Inventor: Rembert Stratmann, Hamburg (DE)

(73) Assignee: DCS Innovative Diagnostik-Systeme Dr. Christian Sartori GmbH & Co. KG, Hamburg (DE)

( * ) Notice: Subject to any disclaimer, the term of this patent is extended or adjusted under 35 U.S.C. 154(b) by 79 days.

(21) Appl. No.: 13/395,481

(22) PCT Filed: Sep. 13, 2010

(86) PCT No.: PCT/DE2010/001073
§ 371 (c)(1),
(2), (4) Date: Mar. 12, 2012

(87) PCT Pub. No.: WO2011/029436
PCT Pub. Date: Mar. 17, 2011

(65) Prior Publication Data
US 2012/0168588 A1 Jul. 5, 2012

(30) Foreign Application Priority Data
Sep. 14, 2009 (DE) .......................... 10 2009 041 140

(51) Int. Cl.
*B65D 19/00* (2006.01)
*G01N 1/31* (2006.01)
*G01N 35/00* (2006.01)

(52) U.S. Cl.
CPC .......... *G01N 1/312* (2013.01); *G01N 35/00029* (2013.01); *G01N 2035/00089* (2013.01)

(58) Field of Classification Search
USPC .................. 356/244; 118/236; 206/455, 456; 359/391, 396; 248/309.1, 346.03; 211/41.1, 41.14; 427/2.13; 435/809; 436/808
See application file for complete search history.

(56) References Cited

U.S. PATENT DOCUMENTS

| | | | | |
|---|---|---|---|---|
| 2,415,480 | A * | 2/1947 | Gassert | 356/39 |
| 3,985,096 | A | 10/1976 | Guimbretiere | |
| 4,207,980 | A * | 6/1980 | Namiki | 206/456 |
| 4,384,193 | A | 5/1983 | Kledzik et al. | |
| 4,501,495 | A | 2/1985 | Faulkner et al. | |
| 4,985,206 | A * | 1/1991 | Bowman et al. | 422/536 |
| 5,090,568 | A * | 2/1992 | Tse | 206/456 |

(Continued)

FOREIGN PATENT DOCUMENTS

| | | |
|---|---|---|
| EP | 1691185 A1 | 8/2006 |
| FR | 1166726 A | 11/1958 |

(Continued)

OTHER PUBLICATIONS

English translation of international preliminary report on patentability dated Mar. 20, 2012.

*Primary Examiner* — Bradley Duckworth
(74) *Attorney, Agent, or Firm* — Patent Central LLC; Stephen A. Pendorf

(57) ABSTRACT

An object support retainer, which allows object supports to be supported stably for automated dyeing processes and at the same time the uncontrolled drainage of reagent by means of capillary currents to be prevented. The device has at least one bearing surface (3) including a longitudinal web (4) and a transverse web (5), b) the underside (9) of the object support (2) comes to lie substantially centered on the longitudinal web (4), and c) the bearing surface (3) has a smooth surface (29) so that the object support (3) is retained by adhesive forces between overflowing treating agent and the underside (9) of both the object support (3) and the smooth surface (29).

17 Claims, 5 Drawing Sheets

(56) References Cited

U.S. PATENT DOCUMENTS

Figure 1:
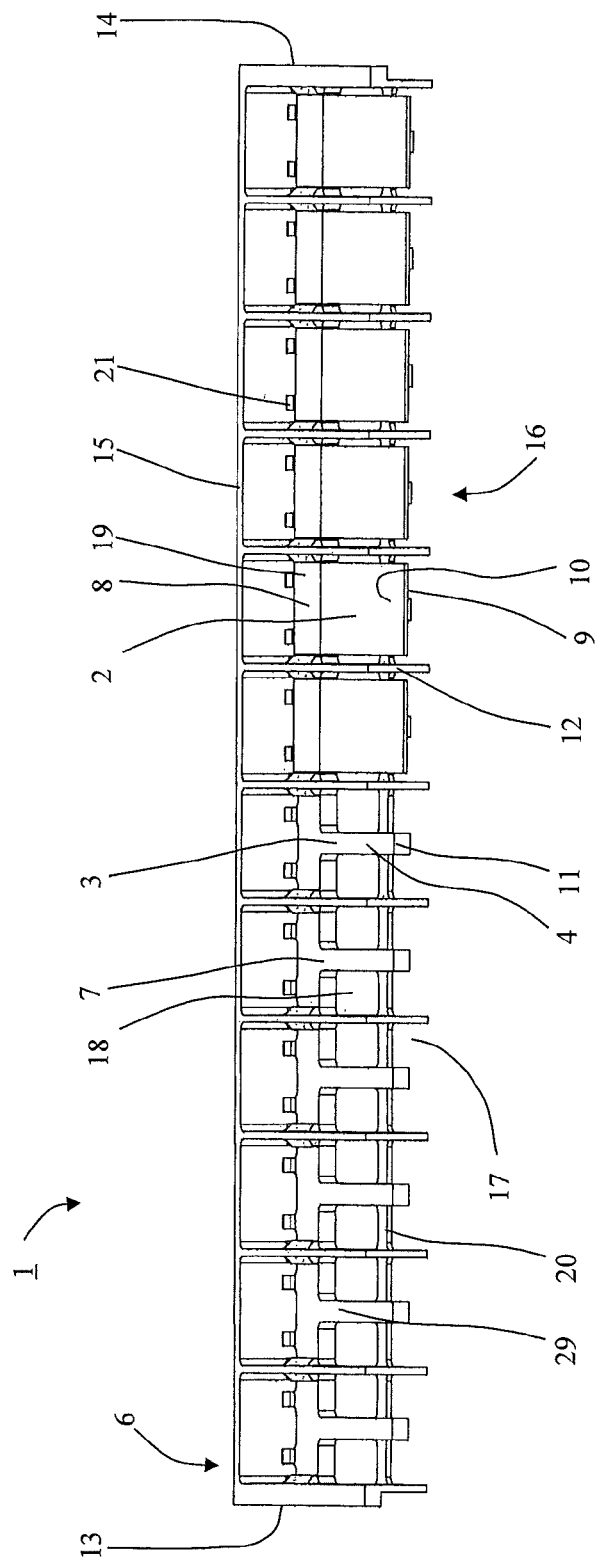

| | | | |
|---|---|---|---|
| 5,192,503 A * | 3/1993 | McGrath et al. | 422/417 |
| 5,411,893 A | 5/1995 | Eden et al. | |
| 5,419,279 A * | 5/1995 | Carrico et al. | 118/406 |
| 6,118,582 A * | 9/2000 | Del Buono | 359/398 |
| 6,703,247 B1 * | 3/2004 | Chu | 436/180 |
| 7,057,808 B2 * | 6/2006 | Dooling | 359/398 |
| 7,678,337 B2 * | 3/2010 | Sage et al. | 422/510 |
| 2003/0217945 A1 | 11/2003 | Kiene et al. | |
| 2005/0270642 A1 * | 12/2005 | McLellan et al. | 359/391 |
| 2007/0109636 A1 * | 5/2007 | Yagi | 359/391 |
| 2011/0266181 A1 * | 11/2011 | Morozov | 206/456 |
| 2012/0002277 A1 * | 1/2012 | Machida et al. | 359/391 |

FOREIGN PATENT DOCUMENTS

| | | |
|---|---|---|
| WO | 9944030 A1 | 9/1999 |
| WO | 9949295 A1 | 9/1999 |
| WO | 2004008106 A2 | 1/2004 |
| WO | 2006116039 A2 | 11/2006 |
| WO | 2009074154 A2 | 6/2009 |

* cited by examiner

OBJECT SUPPORT RETAINER

The invention relates to an object support retainer, in particular for the automated processing of object supports, an arrangement comprising the object support retainer and a method for the automated treatment of a material fixed on an object support.

The processing of object supports with reagents for the dyeing of examination material applied on the object supports is a method which is frequently carried out in modern research and diagnostics. In the prior art, various technologies are by now available in order to treat object supports automatically with reagents.

In the case of such dyes, the material which is to be examined, which is applied on the object support, is incubated in successive steps with a series of reagents, which remain respectively for a particular time on the examination subject, but which subsequently have to be removed again. This takes place for example by rinsing the object support with a buffer excess. A problem here, however, is that an unfavourably configured object support retainer can bring about capillary currents through the wetting with, for example, buffer, which currents lead to the subsequent reagent being removed from the object support and hence from the subject under examination. Thereby, it is for example difficult or even impossible to ensure the necessary maintaining of the intended incubation time for qualitatively high-grade dyes.

Object support retainers are basically known from the prior art. In WO 2004/008106 A2 for example a mounting is disclosed, in which the object support is held with the aid of a clip which clamps the matt edge of the object support (the labelling field). A disadvantage in this is the at least partial covering of the labelling field, which is used through the arrangement of, for example, barcodes, to control dyeing processes in the automation.

U.S. Pat. No. 4,501,495 describes an object support retainer in which the object supports are held with the aid of adhesive strips. In this, it is disadvantageous for example that the adhesive strips have to be regularly renewed. Furthermore, interactions between the adhesive and the reagents can not be ruled out.

In U.S. Pat. No. 4,384,193 an object support retainer is disclosed, in which metal blocks are arranged in a tray, on which metal blocks the object supports are supported. The metal blocks are provided with grooves running transversely, in order to prevent overflowed fluid from being able to bring about the adhesion of the object supports to the metal blocks by capillary effects.

In WO 2006/116039 A2 an object support retainer is disclosed, in which through the formation of a chamber a flowing off of reagent is prevented. This retainer is technically complex and the covering for the chamber formation must be moved with every change of reagent.

From the prior art, object support retainers are also known which propose a solution to the problem described above with regard to the capillary effect. WO 99/49295 discloses, for example, an object support retainer for a stainer, in which object supports rest with their edge on mountings of an insert, which is arranged in the stainer. On the base of the stainer, projections can be provided on which the object supports come to lie on introduction of the insert, so that the edges of the object supports have no contact with the insert in the region in which the reagent is applied. Thereby, the capillary effect which is described above is to be avoided. This solution is relatively complex and is only able to be realized with the especially configured stainer.

Furthermore, from WO 99/44030 an object support retainer is known in which the object support rests with the underside at its corners on specially configured posts, in order to avoid the described capillary effect. A disadvantage in this is, inter alia, the comparatively complicated configuration of the posts.

It is also known to interrupt capillary currents by hydrophobic boundary lines. Here, in preparation for the automation, hydrophobic boundary areas are applied onto the object support, in order to delimit the subject under examination, and to thus cause an interruption of the capillary flow of reagent applied onto the subject under examination. The application of the boundary lines is carried out manually, is laborious and is not reliable in all cases.

It is an object of the present invention to provide an object support retainer which avoids the disadvantages of the prior art, in particular is able to be produced in a simple manner and makes it possible to support object supports for automated dyeing processes in a stable manner and, in so doing, at the same time prevents the uncontrolled flowing off of reagent through capillary currents.

The problem is solved by the subject matter of claim 1. Preferred embodiments of the invention are indicated in the subclaims.

The invention provides an object support retainer, which comprises at least one bearing surface for an object support, wherein
a) the bearing surface has a longitudinal web and a transverse web extending substantially transversely to the longitudinal web,
b) the longitudinal web is arranged in such a way that the underside of the object support comes to lie substantially centered on the longitudinal web, and
c) the bearing surface has a smooth surface at least in a partial area so that the object support is retained during use by adhesive forces between overflowing treating agent and the underside of both the object support and the smooth surface, and/or the bearing surface has a slip-resistant surface at least in a partial area.

"Capillary flow" is understood here to mean the flow of a fluid which is brought about by capillary forces, i.e. by adhesive forces which act between a fluid and a solid. Capillary currents occur in particular at the contact sites of the edge of the upper surface, i.e. facing away from the ground, of the object support with the supporting or respectively retaining device of the object support. However, capillary currents can also occur at the contact sites of the edge of the lower surface (facing the ground) of the object support to the supporting or respectively retaining device of the object support. Through fluid bridges, e.g. drops, to the surface facing away from the ground, a flowing off of reagent from the examination subject can occur.

An "object support" is understood here to mean any support on which an examination material can be applied. It can, for example, be a rectangular glass object support in the form of a glass plate, as is generally used for example in microscopy or respectively histology. Such an object support preferably has the conventional dimensions (26×76 mm×1-1.5 mm) in accordance with ISO 8255-2, but may also have different dimensions. It may also be a plastic object support, a membrane or suchlike, provided that the supports have a sufficient stability.

The "underside" of the object support is understood to mean here the surface of the object support facing the ground, not carrying the examination subject.

"Central" is understood to mean here that the edges of the object support running along the longitudinal web have substantially the same distance to the longitudinal web. In the case of a conventional rectangular microscope object support with narrow and long sides, "central" means, for example, that the longitudinal axis of the object support and the longitudinal axis of the longitudinal web are arranged in the vertical substantially directly one over the other, and the long sides running parallel to the longitudinal web have substantially the same distance to the longitudinal axis of the longitudinal web.

The term "smooth surface" means here a continuously even surface with minimal roughness. In particular, it is understood to mean a surface which enables the formation of a continuous capillary aqueous fluid layer between itself and the underside of a glass object support, so adhesive forces act between the glass object support and the smooth surface, which substantially prevent a movement of the object support contrary to the adhesion forces, i.e. routinely in the vertical.

The term "slip-resistant surface" means, in the context of the present invention, a surface which is constructed so that the object support, on inclination of the object support retainer or of the bearing surface with respect to the horizontal, does not change or only changes its position insignificantly in relation to the object support retainer, to the effect that it slides along the bearing surface, in particular along the longitudinal axis of the longitudinal web. A "slip-resistant surface" is understood here to mean, for example, a surface in which with an inclination through at least 1°, advantageously through at least 2°, 3°, 4°, 5°, 6°, 7°, 8°, 9°, 10°, 12°, 15°, 20°, 25° or 30°, no or only an insignificant slipping of the object support along the bearing surface occurs, in particular along the longitudinal axis of the longitudinal web, with respect to its position in the horizontal. An "insignificant slipping" is to be understood to mean a change in position of the object support in the inclination direction, which is less than 5%, preferably less than 4%, 3%, 2%, 1% or 0.5% of the longitudinal extension of the object support in the inclination direction.

When the term "bearing plane" is used here, this means the plane in which the part of the underside of the object support lies, by which the object support rests on the object support retainer. "Bearing surface" means the surface which is provided for the supporting of the object support.

The present invention makes it possible to keep the surface of the object support on which the examination subject is fixed fully accessible for reagent. This is advantageous because an examination subject, e.g. tissue sections, for technical reasons can not be positioned exactly and therefore if applicable reaches up to the edge of the reaction surface. Reaction surface means here the region of the object support which usually does not serve for identification, i.e. for example not the matt edge or respectively the labelling field. In the object support retainer according to the invention furthermore the matt edge or respectively the labelling field is fully accessible for the automatic data acquisition.

The object support retainer according to the invention also makes possible in particular a stable supporting of the object support in automated dyeing processes. "Stable" means that e.g. in the supply of reagent, the removal of reagent and/or with a transmission of motion through the machine, no or only an only insignificant movement of the object support is brought about with respect to the object support retainer. Coming into question as movements of the object support here are tipping about a longitudinal axis (rolling), tipping about a transverse axis (tilting), rotating about a vertical axis and slipping in the direction of a longitudinal and/or transverse axis. Such object support movements can be effectively avoided with the aid of the object support retainer according to the invention.

A stable retaining of an object support is produced in the object support retainer according to the invention through the particular configuration of the bearing surface. The longitudinal web provides for a stabilisation with regard to the transverse axis of the object support, so that a tilting about the transverse axis is prevented. The transverse web prevents a rolling about the longitudinal axis. The transverse web preferably has a length and a width which prevents an occurrence of a capillary flow. Preferably, the length of the transverse web is smaller than the object support width. However, it can also correspond to the object support width or can exceed this, e.g. in embodiments with an inclined bearing surface. The "length" of the transverse web is understood to mean here its extent in the direction transversely to the longitudinal axis of the longitudinal web; "width" is understood to mean the extent in the direction towards the longitudinal axis of the longitudinal web. Preferably, the length of the transverse web is at least 40%, at least 50%, at least 60%, at least 70% or at least 80%, but a maximum of 90% of the width of the object support. The transverse web can be provided at any desired position along the longitudinal web, but is preferably sufficiently spaced apart from the object support edge, in order to avoid the occurrence of a capillary flow. In a preferred embodiment, the transverse web is situated at one end of the longitudinal web and supports the object support in an edge region, preferably in the region of the matt edge or respectively labelling field, from below. In this embodiment, the bearing surface is substantially T-shaped. The transverse web can, however, also be arranged at a different position along the longitudinal web, so that for example a substantially cruciform configuration of the bearing surface is produced. It is self-evident that if applicable several transverse webs can be provided. A further stabilisation can be additionally produced if applicable in that at the other end of the object support a further transverse web is provided, which may, however, be narrower and if applicable also shorter. It is preferred that the longitudinal web is sufficiently spaced apart from all side edges of the object support, in the case of a rectangular object support therefore also from its narrow sides, in order to prevent a capillary flow. The longitudinal web preferably has a length which corresponds to at least 40%, preferably at least 50%, at least 60%, at least 70% or at least 80%, but a maximum of 90% of the length of the object support. The "length" of the longitudinal web is understood to mean here its extent in the direction of the longitudinal axis, wherein also the section is added to the length which is part of the transverse web. In the case of several transverse webs, all these sections are included for determining the length of the longitudinal web. The ratio of the length of the longitudinal web to the length of the transverse web is preferably 1:1 to 6:1, more preferably 1.2:1 to 5:1, more preferably 1.5:1 to 4:1 and particularly preferably 2:1 to 3:1.

A further stabilisation of the object support, in particular with regard to the tipping about the longitudinal and/or transverse axis, can be achieved in the object support retainer according to the invention by care being taken that when rinsing with water, buffer or suchlike an aqueous fluid film forms between the bearing surface and the underside of the object support, which film, owing to the adhesive forces which occur, brings about an adhesion of the object support to the bearing surface. So that the adhesive forces can be effective over as large an area as possible, the bearing surface is preferably provided with a smooth surface in as large a region as possible. Preferably, the object support retainer according to the invention is therefore configured so that the fluid film forms at least over the region of the longitudinal web. In a preferred embodiment, the object support retainer according to the invention is, however, configured so that the fluid film forms over the entire bearing surface, i.e. also in the region of the transverse web.

The person skilled in the art will readily discern that the transverse web can also be dispensed with entirely, when the longitudinal web is provided in a suitable width which is indeed less than the width of the object support, in order to prevent the occurrence of capillary currents, but which is sufficient to prevent a rolling. The suitable longitudinal web width depends on the object support and can be easily ascertained by the person skilled in the art by routine tests. Preferably, the longitudinal web is equipped here with a slip-resistant surface, as is described in more detail further below.

The bearing surface preferably consists of metal or respectively of a metal alloy, particularly preferably of aluminium. It can, however, also be produced from a suitable plastic. The plastic should be suitable here for a thin fluid film to be able to form between its surface and an object support lying thereon, via which the object support is fixed in an adhesive manner.

Alternatively, or if applicable also additionally, the bearing surface can be provided at least partially with a slip-resistant surface. The bearing surface can be provided here with a slip-resistant surface only in the region of the longitudinal web, either completely or only in a partial region thereof, or also in the region of the transverse web. Such a slip-resistant surface is intended substantially to prevent a slipping of the object support in the direction of a longitudinal and/or transverse axis of the object support and can be produced for example by suitable structuring of the surface or by the arrangement of a slip-resistant material, e.g. a suitable polymer for example an elastic material such as e.g. silicone on or respectively in the bearing surface. The bearing surface, or a part thereof, can be coated for this with a slip-resistant material. A depression can also be provided in the bearing surface, e.g. in the region of the longitudinal web, into which the slip-resistant material is introduced. The choice of a suitable slip-resistant material lies within the skill of the average skilled person and does not require any inventive activity. The material should be as resistant as possible to the reagents which are to be used.

The slip-resistant material is preferably elastic and consists for example of silicone, particularly preferably of soft silicone, e.g. of Shore hardness 30, with a smooth contact surface for the object support. In a preferred embodiment, the slip-resistant surface can be provided only in a limited region of the bearing surface, for example at its end lying opposite the transverse web, preferably within the longitudinal web at the end which is spaced furthest apart from the matt edge or respectively the labelling field, or as part of a second transverse web which is provided if applicable. In such an embodiment, the slip-resistant surface is designated here as a "stopper". The stopper can be configured for example in a circular, square or in any other desired shape, and is arranged so that the object support comes to lie with its end lying opposite the transverse web on the contact surface of the stopper, i.e. the surface of the stopper which comes in contact with the object support. The adhesive forces occurring through the close contact between the stopper and the object support without a fluid film therebetween prevent rotational and/or slipping movements of the object support. Also, several stoppers can be provided. The stopper can be, for example, a silicone stopper, which is introduced into a corresponding recess of the longitudinal web. Preferably, the stopper is configured here so that on removal of the object support, the adhesion forces are overcome, but the stopper remains in the recess of the object support retainer. The stopper can be fixed for example by glueing, screwing, form- and/or force fit. Preferably, the stopper is fixed so as to be detachable.

Preferably, the slip-resistant material projects slightly, for example 0.1 mm, in vertical direction or respectively in a direction facing away from the ground, over the plane of the smooth surface, which preferably comprises the remaining bearing surface, i.e. the part of the bearing surface which is not provided with the slip-resistant material. The adhesive forces acting in the fluid-filled gap between the object support and the smooth surface press the object support onto the slip-resistant material, which is configured for example as a stopper, which material can thereby change its shape, so that for example the contact surface can additionally enlarge and the slip-resistant material can be pressed down by its surface substantially onto the plane of the smooth surface. Hereby, in turn, a reinforcement of the adhesive forces is brought about between the slip-resistant surface and the object support.

The region of the bearing surface comprising the slip-resistant material or respectively the stopper can be lowered beneath the plane formed by the remaining bearing surface. The contact surface of the slip-resistant material can be thereby arranged for example also without the action of adhesive forces at the level of the plane of the remaining bearing surface. Furthermore, for the case where the slip-resistant material projects, the region comprising the slip-resistant material is preferably also configured so that the slip-resistant material can expand e.g. in the case of adhesive forces occurring in the region. This can take place for example such that a portion of the lowered region around the slip-resistant material is kept free of slip-resistant material, so that the slip-resistant material can expand in that direction.

To counteract a slipping of the object support, it is particularly advantageous if the object support, as is preferred, is held by the object support retainer so that it is inclined towards the end of the object support which lies opposite the matt edge or respectively labelling field. In this way, it is avoided that reagent arrives onto the matt edge or respectively the labelling field. Such an inclination can be achieved for example in that in the object support retainer the bearing surface itself is arranged so as to be inclined in a corresponding manner. Alternatively, the object support retainer as a whole can also be inclined.

The stable bearing of the object support which is enabled by the object support retainer according to the invention also enables the targeted movement of the object support, coated with reagent, together with the object support retainer, in order to achieve, through the convection which is thereby produced, a mixing or respectively a better mixing of the reagents and/or a higher reaction speed. The targeted movement can be, for example, a tipping, rotating, shaking or tumbling movement. The object support retainer is set here into a corresponding motion, which is then also carried out by the object support.

According to the invention, capillary currents are prevented by the geometry and arrangement of the longitudinal and transverse webs. The longitudinal web runs beneath the region of the reaction surface of the object support and has a sufficient distance from the edge of the object support facing away from the ground and facing the ground, in order to prevent an occurrence of capillary currents. The transverse web is arranged beneath the matt edge or respectively labelling field and preferably does not extend beneath the region with the reaction surface of the object support. The matt edge or respectively the labelling field prevent the occurrence of capillary bridges between the surface of the object support carrying the object and the bearing surface in the region of the transverse web. An optionally present second transverse web is arranged accordingly so that a sufficient distance is maintained from the object support edges.

Preferably, the object support retainer is configured such that it can receive several object supports. In this case, it is preferred that the bearing surfaces, and hence also the object supports, are arranged in a receiving profile and are separated from each other by suitable means. This can take place for example by walls which are provided between the bearing surfaces.

In a further aspect, the invention also relates to an arrangement which comprises an object support retainer according to the invention and one or more object supports.

In a further aspect, the invention also relates to a method for the automated treatment of a material which is fixed on an object support. In the method according to the invention, the object support is held by an object support retainer, as was described above, treating agent is delivered onto the object support, and the object support retainer is set in motion together with the object support. The motion is preferably a tipping, rotating, shaking or tumbling motion.

The stable supporting of the object support provided by the object support retainer according to the invention makes it possible to set the latter in motion without an appreciable slipping of the object support occurring. The movement of the object support leads to a corresponding movement also of the reagents situated on the object support, and thereby makes the mixing thereof possible or respectively improves the mixing thereof. Thereby, the desired reaction can be made possible and/or can be accelerated.

For the case where several object supports are to be set in motion, e.g. a tumbling motion, it is preferred that the object supports are held respectively separately in object support retainers, instead of arranging them for example in a shared receiving profile. Thereby, a uniform motion of the object supports can be achieved, whereas with arrangement in a shared receiving profile the individual object supports would carry out different motions.

In a preferred embodiment of the method according to the invention, the treating agent is an aqueous medium, preferably an aqueous staining reagent, and the fixed material is a biological specimen, preferably a tissue section or a cell smear. Particularly preferably, the method according to the invention is provided here for use in histology, immunohistochemistry, in situ hybridisation or microarray processing.

Figure 2:
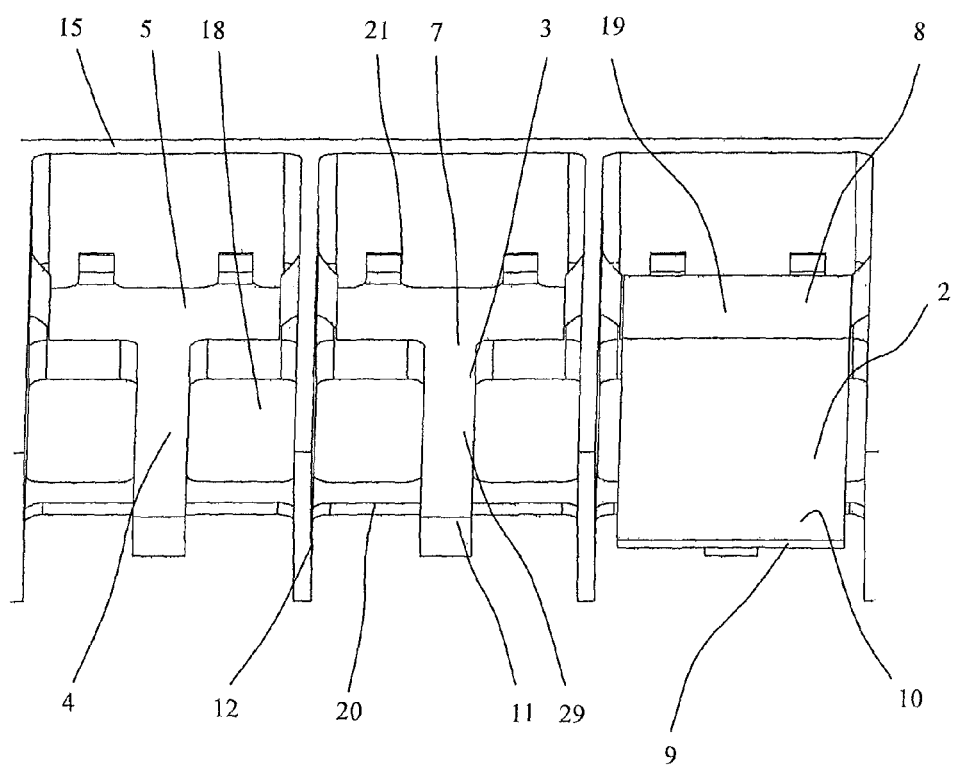
Figure 3:
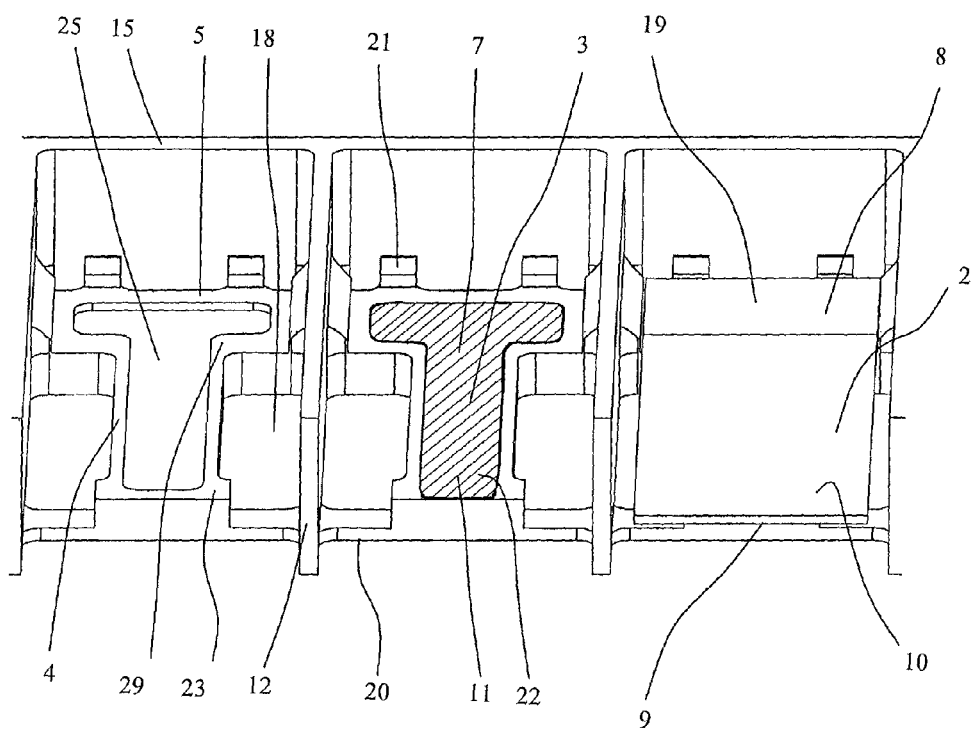
Figure 4:
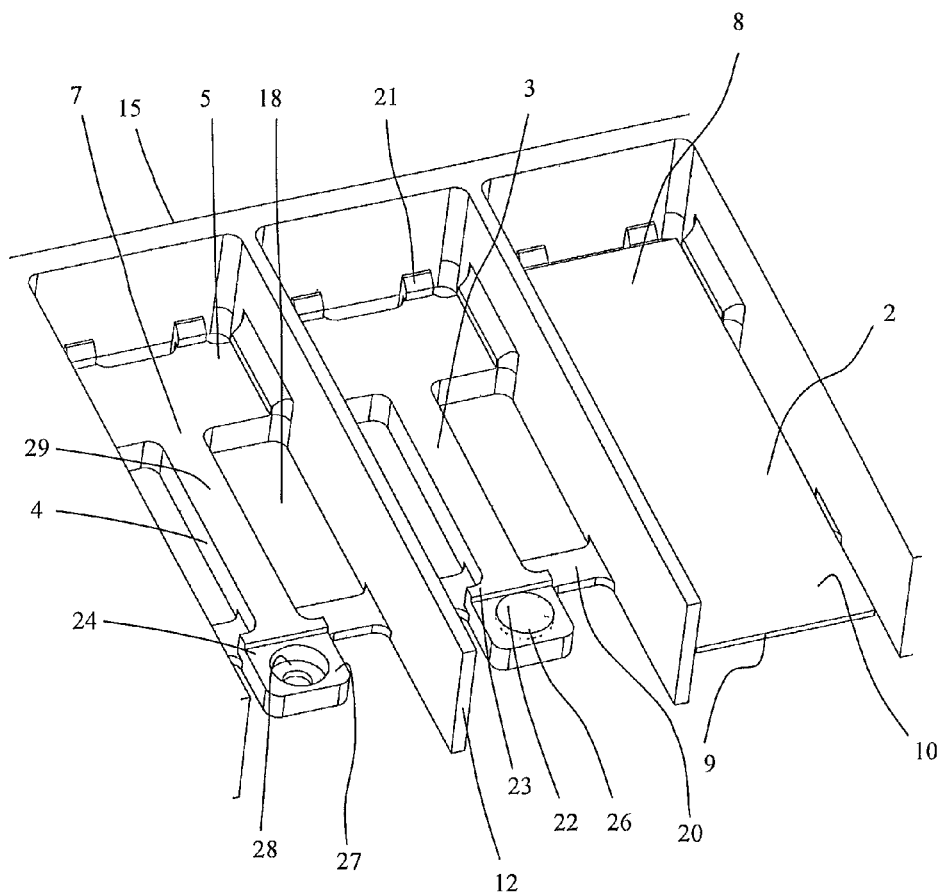
Figure 5:
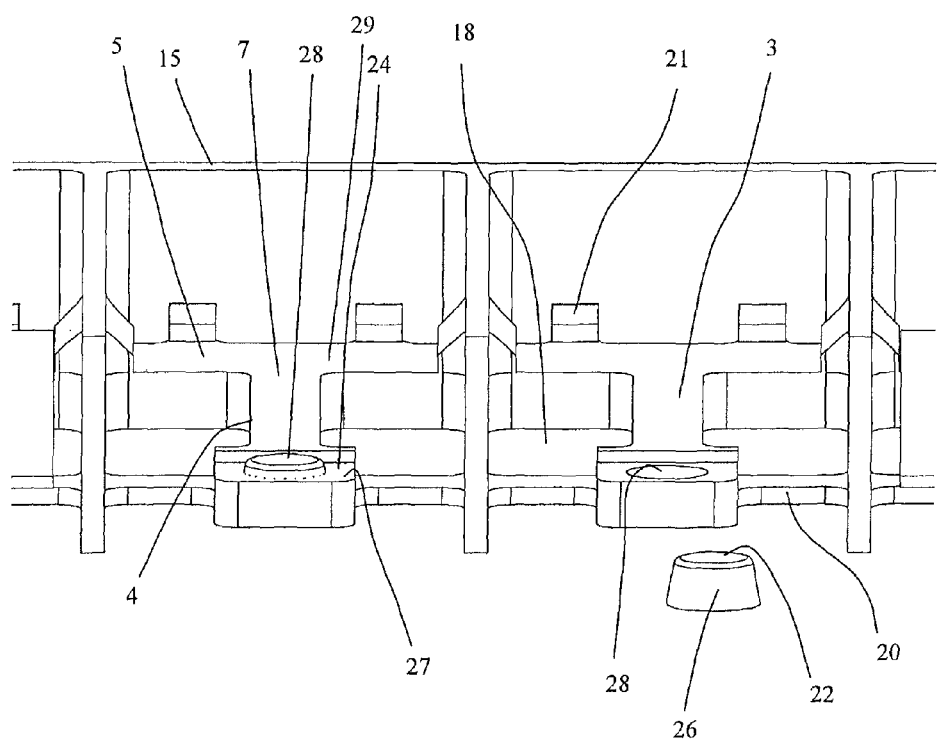

The invention is explained in further detail below, merely for illustration, with the aid of the enclosed figures and preferred embodiments, in which are shown:

FIG. 1 an embodiment of the object support retainer according to the invention, FIG. 2 a portion of the object support retainer illustrated in FIG. 1, FIG. 3 another embodiment of the object support retainer according to the invention, with a slip-resistant surface, FIG. 4 a further embodiment of the object support retainer according to the invention, with a slip-resistant surface in the form of a stopper, FIG. 5 a further illustration of the embodiment of the object support retainer according to the invention illustrated in FIG. 4.

FIG. 1 shows an embodiment of the object support retainer 1 according to the invention. The object support retainer 1 consists here of a receiving profile 6 with outer walls 13, 14 and 15. The receiving profile 6 is open to the side 16 lying opposite the outer wall 15 or respectively the transverse web 5. The bearing surface 3 is configured substantially in a T-shape with a longitudinal web 4 and a transverse web 5. The longitudinal web 4 stands substantially vertically on the transverse web 5 and extends from its centre in the direction of the open side 16 of the receiving profile 6. The transverse web 5 is arranged towards the outer wall 15 of the receiving profile 6. The transverse web 5 and the longitudinal web 4 form a continuous smooth surface 29. Several bearing surfaces 3 are provided, of which six (in the left-hand portion of FIG. 1) are illustrated without object support 2 and six with object support 2. The object supports 2 lie substantially centrally with their underside 9 and, with the exception of the region resting on the transverse web 5, with their entire length on the longitudinal web 4. Furthermore, the object supports 2 lie in the region of the edge surface 8 with their underside 9 on the transverse web 5. The upper side 10 of the object supports 2 is provided with the examination subject. The bearing surfaces 3 are separated from each other by walls 12, so that an overflow of fluid from an object support 2 onto an adjacent object support 2 or respectively a spray contamination is prevented. The base 17 of the receiving profile 6 is not fully closed. Rather, between the walls 13, 14 or respectively the walls 12 and the longitudinal webs 5, openings 18 are formed through which buffer and suchlike can flow off. The matt edge or respectively the labelling field 19 of the object supports is freely accessible. The longitudinal webs 4 are connected in the region of their end 11 with the walls 12, 13, 14 via supporting webs 20.

FIG. 2 shows a cutout of FIG. 1. Here, mountings 21 can be seen more clearly, which form an abutting surface here for the object supports 2.

FIG. 3 shows another embodiment of the object support retainer 1 according to the invention. The bearing surface 3 has a slip-resistant surface 22 here in the region of the longitudinal web 4 and of the transverse web 5. This is a T-shaped silicone mat here, which is introduced into a recess 25. Furthermore, at the end 11 of the longitudinal web 4 situated to the open side 16 of the receiving profile 6, a second transverse web 23 is provided, which is, however, constructed to be narrower than the transverse web 5 and also has shorter legs. The second transverse web 23 is connected with supporting webs 20 with the respectively adjacent walls 12, 13, 14.

FIG. 4 shows a portion of a further embodiment of the object support retainer 1 according to the invention. In this embodiment of the object support retainer 1, a slip-resistant surface 22 in the form of a stopper 26 is provided to the open side 16 of the receiving profile 6. The stopper 26 is produced from soft silicone and is introduced by its base into a recess 28 in a partial area 24 of the bearing surface 3. A second transverse web 23 is provided towards the transverse web 5. The partial area 24 of the bearing surface 3 encompassing the stopper 26 is lowered under the remaining surface of the bearing surface 3, on which the object support 2 rests with its underside 9. The stopper 26 projects beyond the plane of the surface 27 of the partial area 24, so that the slip-resistant surface 22 projects into the plane formed by the remaining portion of the bearing surface 3 or slightly over it. The object support 2 lies in the insert on the portion of the bearing surface 3 which is not lowered, and on the stopper 26. In an embodiment in which the slip-resistant surface 22 still projects beyond the plane of the non-lowered portion of the bearing surface 3, the stopper 26 is compressed by adhesive forces which act between the bearing surface 3 and the underside 9 of the object support 2, when a fluid film is present there, e.g. through overflowing buffer, so that the slip-resistant surface 22 comes to lie in the plane of the non-lowered portion of the bearing surface 3. The portion of the stopper 26 which is not situated in the recess 28 expands here in the adjacent free space.

In FIG. 5, the embodiment of the object support retainer 1 according to the invention, illustrated in FIG. 4 is illustrated from a different perspective. In the right-hand portion of the illustration, a stopper 26 is illustrated which has been removed from the recess 28.

LIST OF REFERENCE NUMBERS 1 object support retainer
2 object support
3 bearing surface
4 longitudinal web
5 transverse web
6 receiving profile
7 end
8 edge surface
9 underside of the object support
10 upper side (specimen side) of the object support
11 end
12 wall
13 outer wall of the receiving profile
14 outer wall of the receiving profile
15 outer wall of the receiving profile
16 side
17 base of the receiving profile
18 opening
19 matt edge/labelling field
20 supporting web
21 mountings
22 slip-resistant surface
23 second transverse web
24 partial area
25 recess
26 stopper
27 surface
28 recess
29 smooth surface

The invention claimed is:

1. An object support retainer (1) comprising at least one bearing surface (3) adapted for supporting an object support (2) by capillary action, the object support to be supported having an underside with a smooth surface at least in part, wherein
   a) the bearing surface (3) comprises a longitudinal web (4) and a transverse web (5) extending substantially transversely to the longitudinal web (4),
   b) the longitudinal web (4) is arranged in such a way that the underside (9) of an object support (2) placed thereon comes to lie substantially centered on the longitudinal web (4) and wherein the longitudinal web (4) is narrower than an object support (2) such that the longitudinal web (4) is spaced apart from edges of an object support (2) placed thereon running along the longitudinal web (4), and
   c) the bearing surface (3) comprises at least one of
      a smooth surface (29), wherein the bearing surface (3) smooth surface (29) is sized and oriented to contact the smooth underside area of an object support (2) placed thereon so that bearing surface (3) is capable of forming a continuous aqueous fluid layer by capillary action and retaining an object support (2) during use by the capillary adhesive forces between the underside (9) of the object support (2) and the smooth surface (29) of the bearing surface (3), such that a movement of the object support (2) contrary to the capillary adhesive force is substantially prevented, and
      a slip-resistant surface (22).

2. The object support retainer according to claim 1, wherein the bearing surface (3) is configured substantially in a T-shape, so that an object support (2) placed thereon comes to lie with an edge surface (8) of its underside (9) on the transverse web (5).

3. The object support retainer according to claim 1, wherein the slip-resistant surface (22) is produced by a slip-resistant material arranged on or in the bearing surface (3), and the slip-resistant material is arranged at least in the region of the longitudinal web (4).

4. The object support retainer according to claim 3, wherein the slip-resistant material is arranged on the end of the bearing surface (3) lying opposite the transverse web (5) in a partial area (24) of the bearing surface (3).

5. The object support retainer according to claim 3, wherein the slip-resistant material (22) projects only so far over the plane of the smooth surface (29) that the surface of the slip-resistant material (22) in use is pressed down substantially onto the plane of the smooth surface (29) owing to the weight of the object support (2) and the adhesive forces acting between the smooth surface (29) and the object support (2) due to overflowing treatment agent.

6. The object support retainer according to claim 3, wherein the slip-resistant material is an elastic slip-resistant material.

7. The object support retainer according to claim 3, wherein the slip-resistant material is silicone.

8. The object support retainer according to claim 1, wherein in a receiving profile (6) a plurality of bearing surfaces (3) is provided, which are separated from each other by walls (12).

9. An arrangement comprising an object support retainer (1) according to claim 1 and one or more object supports (2).

10. An object support retainer (1) comprising at least one bearing surface (3) adapted for supporting an object support (2) by capillary action, the object support to be supported having an underside with a smooth surface at least in part, wherein
   a) the bearing surface (3) comprises a longitudinal web (4) and a transverse web (5) extending substantially transversely to the longitudinal web (4),
   b) the longitudinal web (4) is arranged in such a way that the underside (9) of an object support (2) placed thereon comes to lie substantially centered on the longitudinal web (4) and wherein the longitudinal web (4) is narrower than an object support (2) such that the longitudinal web (4) is spaced apart from edges of an object support (2) running along the longitudinal web (4), and
   c) the bearing surface (3) comprises a smooth surface (29) at least in a partial area, wherein the bearing surface (3) smooth surface (29) is sized and oriented to contact the smooth underside area of an object support (2) placed thereon so that bearing surface (3) is capable of forming a continuous aqueous fluid layer by capillary action and retaining an object support (2) during use by the capillary adhesive forces between the underside (9) of the object support (2) and the smooth surface (29) of the bearing surface (3), such that a movement of the object support (2) contrary to the capillary adhesive force is substantially prevented, and the bearing surface (3) comprises a slip-resistant surface (22),
      wherein the slip-resistant surface (22) is produced by a slip-resistant material arranged on or in the bearing surface (3), and the slip-resistant material is arranged at least in the region of the longitudinal web (4), and wherein the slip-resistant material is arranged in a recess (28) on the end of the bearing surface (3) lying opposite the transverse web (5).

11. The object support retainer according to claim 10, wherein the recess (28) is arranged in a partial area (24) of the bearing surface (3), the partial area (24) being lowered with respect to the plane formed by the surfaces of the longitudinal web (4) and of the transverse web (5).

12. An object support retainer (1) comprising at least one bearing surface (3) adapted for supporting an object support (2) by capillary action, the object support to be supported having an underside with a smooth surface at least in part, wherein
  a) the bearing surface (3) comprises (aa) a longitudinal web (4) having a first end (7) and a second end (11), and (ab) a transverse web (5) extending substantially transversely to the longitudinal web (4),
  b) the longitudinal web (4) is arranged in such a way that the underside (9) of an object support (2) placed thereon comes to lie substantially centered on the longitudinal web (4) and wherein the longitudinal web (4) is narrower than an object support (2) such that the longitudinal web (4) is spaced apart from edges of an object support (2) running along the longitudinal web (4), and
  c) the bearing surface (3) comprises at least one of
    a smooth surface (29), wherein the bearing surface (3) smooth surface (29) is sized and oriented to contact the smooth underside area of an object support (2) placed thereon so that bearing surface (3) is capable of forming a continuous aqueous fluid layer by capillary action and retaining an object support (2) during use by the capillary adhesive forces between the underside (9) of the object support (2) and the smooth surface (29) of the bearing surface (3) such that a movement of the object support (2) contrary to the capillary adhesive force is substantially prevented, and
    a slip-resistant surface (22),
    wherein the bearing surface (3) is inclined towards the second end (11) of the longitudinal web (4) lying opposite the first end (7) of the longitudinal web (4).

13. A method for the automated treatment of a material fixed on an object support, the object support having an underside with a smooth surface at least in part, comprising
  placing the object support underside smooth surface on an upward facing bearing surface smooth surface of an object support retainer according to claim 1,
  supplying treating agent onto the object support in an amount sufficient to flow to the area of contact between the object support retainer and the object support, to form a continuous aqueous fluid layer between the underside smooth surface of the object support and the bearing surface smooth surface, and cause capillary action sufficient to retain the object support on the object support retainer during automated treatment, such that a movement of the object support (2) contrary to the capillary adhesive forces is substantially prevented, and
  setting the object support retainer in motion together with the object support.

14. The method according to claim 13, wherein the object support retainer is set into a tipping, rotating, shaking or tumbling motion.

15. The method according to claim 13, wherein an aqueous medium is used as treating agent, and the fixed material is a biological specimen.

16. The method according to claim 15, wherein an aqueous medium is aqueous staining reagent.

17. The method according to claim 15, wherein the fixed material is a tissue section or a cell smear.

* * * * *